(12) United States Patent
Pliszka

(10) Patent No.: US 8,398,962 B2
(45) Date of Patent: *Mar. 19, 2013

(54) LIQUID SEALANT AND METHODS OF USE

(75) Inventor: Matthew E. Pliszka, Mequon, WI (US)

(73) Assignee: Environmentally Sensitive Solutions, Inc., Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/534,577

(22) Filed: Jun. 27, 2012

(65) Prior Publication Data

US 2012/0269759 A1 Oct. 25, 2012

Related U.S. Application Data

(63) Continuation of application No. 13/179,286, filed on Jul. 8, 2011, now Pat. No. 8,231,865, and a continuation of application No. 11/366,642, filed on Mar. 2, 2006, now abandoned.

(60) Provisional application No. 60/657,751, filed on Mar. 2, 2005.

(51) Int. Cl.
*A61L 9/012* (2006.01)

(52) U.S. Cl. .......................................... 424/76.1; 4/321

(58) Field of Classification Search ................. 424/76.1
See application file for complete search history.

(56) References Cited

U.S. PATENT DOCUMENTS

| | | | |
|---|---|---|---|
| 303,822 A | 8/1884 | D'Heureuse | |
| 1,050,290 A | 1/1913 | Posson | |
| 3,563,767 A | 2/1971 | Wasserman et al. | |
| 3,829,909 A | 8/1974 | Rod et al. | |
| 4,028,747 A | 6/1977 | Newton | |
| 4,411,286 A | 10/1983 | Ball | |
| 4,773,441 A | 9/1988 | Biba | |
| 5,420,229 A | 5/1995 | Burke et al. | |
| 5,598,777 A | 2/1997 | DeMoore et al. | |
| 5,711,037 A | 1/1998 | Reichardt et al. | |
| 5,752,548 A | 5/1998 | Matsumoto et al. | |
| 6,053,197 A | 4/2000 | Gorges | |
| 6,353,944 B1 | 3/2002 | Clayton | |
| 6,425,411 B1 | 7/2002 | Gorges | |
| 6,487,731 B1 | 12/2002 | Houde | |
| 6,503,077 B2 | 1/2003 | Orth et al. | |
| 6,589,440 B2 | 7/2003 | Atwill | |
| 6,644,339 B2 | 11/2003 | Gorges et al. | |
| 6,701,541 B2 | 3/2004 | Romagna et al. | |
| 6,797,683 B2 | 9/2004 | Shana'a | |
| 2002/0038474 A1 | 4/2002 | Atwill | |
| 2002/0069913 A1 | 6/2002 | Gorges | |
| 2002/0120981 A1 | 9/2002 | Gorges | |
| 2002/0166162 A1 | 11/2002 | Romagna et al. | |
| 2003/0089397 A1 | 5/2003 | Gorges | |
| 2003/0171231 A1 | 9/2003 | Shana'a et al. | |

FOREIGN PATENT DOCUMENTS

| | | |
|---|---|---|
| CA | 2599962 | 4/2011 |
| GB | 2440843 | 12/2009 |
| WO | WO9425693 | 11/1994 |
| WO | WO9629979 | 10/1996 |
| WO | WO9838267 | 9/1998 |
| WO | WO02056817 | 7/2002 |

OTHER PUBLICATIONS

UK Search report; Nov. 20, 2008, of Application No. GB0717236.4.
PCT Search report; of International Application No. PCT/US06/07430.
UK Search report; Jul. 1, 2009, of Application No. GB0717236.4.

*Primary Examiner* — Jake M. Vu

(74) *Attorney, Agent, or Firm* — Brian G. Gilpin; Jennifer L. Gregor; Godfrey & Kahn, S.C.

(57) ABSTRACT

The invention provides a composition useful for forming odor suppressing seals in waterless urinals. Methods of using the composition to form liquid seals as well as waterless urinals employing such liquid seals are further provided.

13 Claims, 1 Drawing Sheet

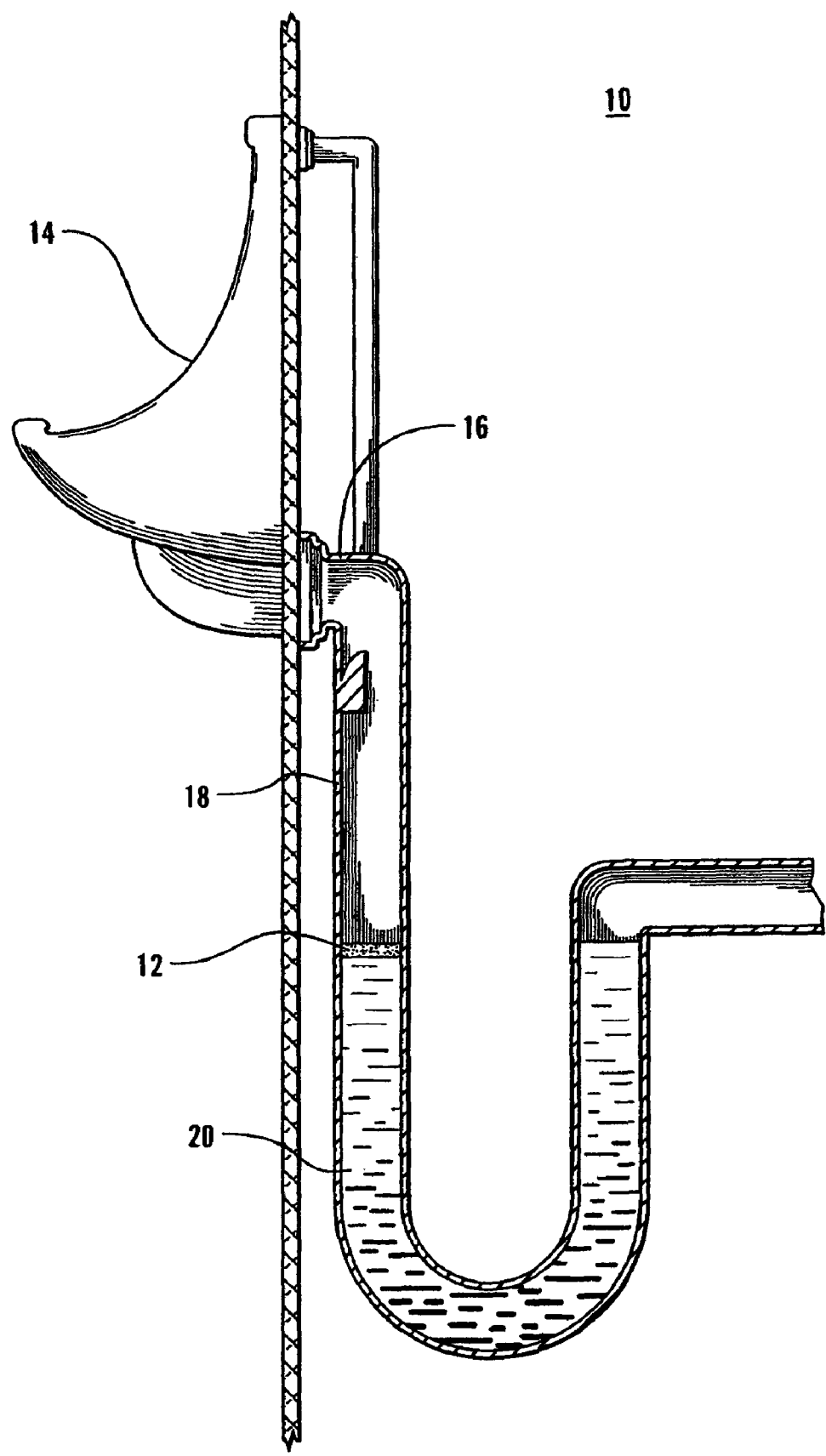

LIQUID SEALANT AND METHODS OF USE

CROSS REFERENCE TO RELATED APPLICATIONS

This application is a continuation of and claims the benefit under 35 U.S.C. §120 of U.S. application Ser. No. 13/179,286, filed Jul. 8, 2011, now U.S. Pat. No. 8,213,865 and U.S. application Ser. No. 11/366,642, filed Mar. 2, 2006, now abandoned which claim priority under 35 U.S.C. §119 to U.S. Provisional Application No. 60/657,751, filed Mar. 2, 2005. The foregoing applications are specifically incorporated herein by reference for all purposes.

FIELD OF THE INVENTION

The present invention is directed to liquid sealants, and more particularly to the use of liquid sealants for odor suppression in waterless urinals.

BACKGROUND OF THE INVENTION

Waterless urinals are becoming more widely used because of costs savings attributed to conservation of water. These waterless devices are not flushed with water each time a person uses them. As the waterless urinal is repeatedly used, urine is collected in a compartment of the urinal, typically a plumbing trap where the volume of urine prevents the escape of sewer gases built up on the sewer side of the trap. A sealing liquid that is immiscible with the urine and is lighter than the urine covers the collected urine. This sealing liquid floats on the surface of the urine, serving as a barrier that prevents odors from the urinal escaping to the environment. In certain embodiments, such waterless urinals include a removable cartridge having a top with an opening therein in communication with a compartment. Such cartridges hold a sealing liquid that allows passage of urine into the compartment, through the sealing liquid. In certain designs, a stand pipe type drain is in communication with the compartment that allows the compartment to be drained continually to a sewer or other waste disposal system as the compartment is filled with urine.

With increasing emphasis on water conservation, there is continuing interest in toilets and urinals designed to minimize the amount of water consumed in flushing, to mitigate excessive demands on both water supplies and wastewater disposal systems, both of which have become overloaded with increasing populations. Unfortunately, waterless toilets and urinals often leave a user with an unpleasant experience because of the malodorous smell of urine reaching the user due to ineffective drain trap means, whether those means are mechanical, chemical, or a combination of both. Overcoming such drawbacks is highly desirable to urinal retailers and manufacturers and, as well, to those concerned with resource conservation.

U.S. Pat. No. 303,822 (D'Heureuse) discloses a wastewater pipe S-trap into which a disinfectant or deodorizer is introduced. The use of an oil as a re-circulated flushing medium in a toilet system is disclosed in U.S. Pat. No. 3,829,909 (Rod, et al.). The use of oil in toilets to form an odor trap is disclosed in German Patent No. 121356 (Beck, et al.) and in U.S. Pat. Nos. 1,050,290 (Posson) and 4,028,747 (Newton). Other examples of oil-sealed traps are found in German Patent No. 2816597.1, and Swiss Patent No. 606,646 (Ernst). In addition, various odor seals for waterless urinals are disclosed in the following references: U.S. Pat. No. 6,425,411 to Gorges; U.S. Pat. No. 5,711,037 to Reichardt et al.; U.S. Pat. No. 6,053,197 to Gorges; U.S. Pat. No. 6,644,339 to Gorges et al.; U.S. Pat. No. 6,701,541 to Romagna et al.; and U.S. Patent Application Publication No. US2003/0089397 A1.

Although various liquid sealants useful for odor suppression have been previously-described, there remains a need in the art for liquid sealants possessing odor suppressing qualities for use in drain traps, particularly in waterless urinals.

SUMMARY OF THE INVENTION

In accordance with the foregoing discussion, the present invention takes the form of a liquid sealant useful in a waterless urinal which includes a gellant, a glyceride and, optionally, various additives. The gellant in the liquid sealant is preferably a polyamide-based gellant, which can be present in the amount of about 1 to about 50 weight percent of the liquid sealant. The glyceride is preferably in the form of a vegetable oil selected from the group consisting of almond oil, canola oil, corn oil, cottonseed oil, flaxseed oil, grape seed oil, olive oil, palm oil, peanut oil, safflower oil, sesame oil, soybean oil, sunflower oil, walnut oil, and mixtures thereof. The amount of glyceride is from about 50 to about 99 weight percent of the liquid sealant.

Liquid sealants according to the invention may also include various additives, such as odor control agent, fragrance, preservative, anti-stick agent, soluble dye, or any combination (blend) thereof. Such optional additives individually comprise from a trace amount to about 10 weight percent of the liquid sealant.

In another embodiment, the invention provides a waterless urinal including a compartment holding collected urine, the improvement comprising a liquid sealant floating on the urine, the liquid sealant formulated as described and claimed herein.

The present invention also encompasses a method of suppressing odors from a waterless urinal including a compartment holding urine, wherein a liquid sealant of the invention is placed in the urinal compartment such that an odor suppressing seal is provided.

In one embodiment, the invention is a method of making a liquid sealant more efficient. In this embodiment, an amount of gellant is added to a liquid seal to set the viscosity of the liquid seal to between about 100 and about 1000 centipoise thereby increasing the effectiveness of the liquid sealant in containing odors emanating from a urinal.

Other objects, features and advantages of the present invention will become apparent after review of the specification, claims and drawings.

BRIEF DESCRIPTION OF THE DRAWING

FIG. 1 is a perspective view of a waterless urinal with a partial cut-away through the trapway illustrating a liquid seal according to the present invention.

DETAILED DESCRIPTION OF THE INVENTION

As shown in FIG. 1, a waterless urinal 10 of this invention utilizes a novel sealing liquid 12. In a preferred embodiment, the urinal 10 includes a bowl 14 with a tapered lower portion 16 that has an outlet tube, or trapway, 18 extending there from that effectively forms a holding compartment. Tube 18 may be connected to an additional holding tank or, optionally, a sewer (not shown). As one of skill will realize upon reading the present disclosure, practice of the invention is not limited to any one particular waterless urinal design, let alone to any specific manufacturer's product line.

Depending on the waterless urinal manufacturer's trapway design, the sealing liquid 12 forms an annular layer about 1 inch to about 6 inches in thickness that floats on top of an initial charge of water 20 or, as the urinal 10 is used, collected urine, or a mixture of water and urine. In preferred embodiments, the layer formed by the sealing liquid will be about 2.5 inches in thickness in a typical trapway design with a 1.5 inch pipe diameter. As used herein, the terms "liquid sealant" and "sealing liquid" are used interchangeably and considered to be equivalent terms.

A liquid sealant according to the present invention includes a gellant and a glyceride. As used herein, the term "gellant" refers to a composition which, when combined with a solvent, forms a colloid in which the disperse phase has combined with the continuous phase. The gellant in the sealing liquid is preferably a polyamide-based gellant, which can be present in the amount of about 1 to about 50 weight percent of the sealant. A preferred polyamide-based gellant is available from Arizona Chemicals, under the registered trademark SYLVAGEL 5000 which, in a most preferred embodiment, is present at about 4 weight percent of the sealant. Other suitable oil or solvent soluble gellants or thickeners include, but are not limited to, diethanolamides, ceteryl alcohols, and aluminum stearates.

The glyceride present in a sealing liquid according to the invention is preferably in the form of a vegetable oil, selected from the group consisting of almond oil, canola oil, corn oil, cottonseed oil, flaxseed oil, grape seed oil, olive oil, palm oil, peanut oil, safflower oil, sesame oil, soybean oil, sunflower oil, walnut oil, and mixtures thereof. As used herein, the term "glyceride" refers to an ester of glycerol and fatty acids in which one or more of the hydroxyl groups of the glycerol have been replaced by acid radicals. The latter may be identical or different so that the glyceride may contain up to three different acid groups. Glycerides can be of natural or synthetic origin with the most common glycerides based on fatty acids (e.g., $C_{14}$ to $C_{18}$) that occur naturally in oils and fats. The term "vegetable oil" refers to oil extracted from the seeds, fruit, or nuts of plants that contains glycerides. The amount of glyceride useful in the invention is from about 50 to about 99 weight percent of the liquid sealant. In a most preferred embodiment, canola oil at about 90 weight percent is present in the sealant. Suitable canola oil (food grade) is available from, for example, AG Environmental Products LLC.

Liquid sealants according to the invention will have a viscosity of between about 100 and about 1000 centipoise, preferably about 400 centipoise, determined using a Brookfield viscometer DV-E at 12 rpm with a #3 spindle. As well, sealants will have a specific gravity from about 0.70 to about 0.99, preferably about 0.88 relative to water. Acceptable flash points for sealants according to the invention range from about 200° F. to about 500° F., most preferably around 330° F.

The liquid sealant according to the invention may optionally include various additives, such as an odor control agent, fragrance, preservative, anti-stick agent, oil soluble dye, or any combination (blend) thereof. If present, each of these additives will individually comprise from a trace amount to about 10 weight percent of the liquid sealant. As used herein, a "trace amount" shall refer to a constituent present in minute fractions of 1 weight percent (1000 ppm or less).

A preferred odor control agent is available from Dow Chemical under the tradename DOWACIDE. The DOWACIDE odor control agent is preferably present at 1 weight percent of the sealant. Additional odor control agents suitable for use include, but are not limited to, triazines, hydantoins, and parabens.

A preferred fragrance is a pine oil available from, for example, Hydrite Chemical. The pine oil fragrance is preferably present at 1.9 weight percent of the sealant. Alternative fragrances include, for example, other terpenes.

A preferred preservative is methyl ethyl paraben (MEPB) available from Hydrite Chemical. The MEPB is preferably present at about 1 weight percent of the sealant. Other alternative preservatives include, but are not limited to, triazines and hydantoins.

A preferred anti-stick agent is a silicone oil available from Trans-Chemco, Inc. under the tradename Trans SF-350. The silicone oil is preferably present at 2 weight percent of the sealant. Alternative anti-stick agents include, but are not limited to, lecithin and waxes.

A preferred soluble dye is an oil soluble green dye available from Keystone under the tradename Liquid Oil Green 1M. The preferred green dye is present at about 0.1 weight percent of the sealant. Other suitable dyes include equivalent oil soluble dyes of other colors.

Specific examples of formulations for the liquid sealant where the ingredients are combined together by weight percentages are set forth in the examples.

The present invention also provides a method of suppressing odors from a waterless urinal including a compartment holding urine, wherein different types and blends of the above-described sealant that float on the urine, with or without additives, are placed in the urinal compartment. An individual may pour liquid sealant into a waterless urinal in an amount sufficient to form an effective seal over the initial water charge and/or urine present in the outlet tube (trapway) of the urinal. As used herein, an "effective" seal or "effective" amount shall refer to a seal or amount of sealant according to the invention that suppresses at least the odor of ammonia gas to a statistically significant degree, as determined by at least the methodologies relied on in Example 2.

A predetermined volume of liquid sealant to form an effective seal is determined by knowledge of the outlet tube's circumference which is directly related to the volume of liquid sealant necessary to form an annular layer about 1 to about 6 inches thick. For example, for an outlet tube (trapway) of tubular design being 1.5 inches in diameter, a volume of about 2 to 6 fluid ounces liquid sealant according to the invention is added to the urinal trapway in order to form a suitable odor suppressing seal. In a preferred embodiment, the liquid sealant is offered with instructions, either on a container or accompanying packaging, which provides a quick reference for the volume of liquid sealant necessary to achieve a suitable seal for various makes and models of waterless urinals and trapway designs.

A further advantage of this invention over prior seals is in regard to cleaning and regenerating an effective odor-suppressing seal. Instead of replacing canisters or cartridges, a custodial engineer may apply a flushing action via, for example, a stream of water directed into the outlet tube to purge an existing seal. A new seal according to the invention is then formed by pouring an effective amount of sealant into the outlet tube.

The examples below are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Liquid Sealant Formulations

A preferred liquid sealant formulation according to the invention follows as Formulation I ("F-I"):

| | |
|---|---|
| Canola oil: | 90 weight percent |
| SYLVAGEL 5000: | 4 weight percent |
| DOWACIDE: | 1 weight percent |
| MEPB: | 1 weight percent |
| Silicone oil: | 2 weight percent |
| Pine oil fragrance: | 1.9 weight percent |
| Oil soluble green dye: | 0.1 weight percent |
| TOTAL: | 100 weight percent |

An alternative liquid sealant formulation follows as Formulation II (F-II):

| | |
|---|---|
| Corn oil: | 90 weight percent |
| SYLVAGEL 5000: | 4 weight percent |
| DMDM Hydantoin: | 1 weight percent |
| MEPB: | 1 weight percent |
| Lecithin: | 2 weight percent |
| D-limonene fragrance: | 1.9 weight percent |
| Oil soluble red dye: | 0.1 weight percent |
| TOTAL: | 100 weight percent |

Example 2

Comparison of Various Liquid Sealants for Use in Suppressing Odors Associated with Waterless Urinals To compare the effectiveness of commercially-available waterless urinal seals against the liquid sealant of the present invention, each liquid sealant was put through separate efficacy tests to measure odor suppressing characteristics. Each test utilized ammonia (ammonia gas as the trace odiferous element representing urine) that the seal must prevent from escaping the liquid sealant surface. Ammonia seepage was detected using a photo ionization detector (PID) meter and color diffusion tubes specific for ammonia gas.

A first test used to determine the effectiveness of urinal seals is the stagnant seal test. The stagnant seal test determines a seal's ability to prevent ammonia seepage through the seal without induced disturbance to the seal. This test simulates the conditions when a waterless urinal sits unused for a few minutes. This test utilized the PID meter for ammonia detection and the test was performed with 25 ml and 15 ml of sealing liquid overlying 200 ml of distilled (stagnant) water in a 250 ml Erlenmeyer flask. Ammonia was introduced into stagnant water under each liquid seal. In order to make the laboratory test more sanitary for the workers involved, store bought ammonia solution was used as a substitute for actual urine. Ammonia is a relevant test solution because ammonia gas is a component of stagnant urinals and is often one of the contributing gases to the undesirable urine smell. Ammonia gas can be selectively detected using commercially available detection devices like a PID meter and color diffusion tubes. One ml of ammonia solution was added to 200 ml of water, and the ammonia gas seepage into flask head space was measured using a PID meter. PID calibration was certified prior to use and all ammonia readings were collected after zeroing the PID meter to the seal's baseline reading. Peak readings were observed, recorded and data logged by the PID meter. The liquid seal layer thickness was made less than optimal in order to test the liquid seal's maximum odor prevention ability.

A second test used to test the effectiveness of a waterless urinal seal is the seal rupture test. The seal rupture test determines a seal's ability to repair itself and prevent seepage of ammonia through the seal. The seal rupture test was set-up similarly to the stagnant seal test using a 250 ml Erlenmeyer flask containing 200 ml of water and 1 ml of ammonia. Water streamed from a water bottle represented a urine stream that would disrupt the seal to simulate urinal use. This test utilized the PID meter for ammonia detection. This test was performed with 25 ml and 15 ml of sealing liquid. The stagnant seal was ruptured using the water stream from a water bottle in order to simulate a urine stream. This experiment investigates the seal's ability to repair itself from abrupt rupture. After rupturing the seal, the ammonia released into the head space was measured using a PID meter. Peak readings were observed, recorded and the test data was logged.

TABLE I gives the data derived from the stagnant seal test and seal rupture test. Data representing ammonia in parts per million released in experiments utilizing 15 ml of each of the respective sealing liquids including the most preferred of Formulation I (F-I) described in Example 1 above is given. A liquid sealant available under the registered trademark DURAVIT®; a liquid sealant available under the trade name URILOCK®; a liquid sealant available under the registered trademark FALCON and a liquid sealant available under the registered trademark BLUESEAL® (the BLUESEAL® product was unstable in all tests giving high readings indicative of volatile nitrogen-based organic compounds). TABLE II gives the data obtained in analogous experimentals utilizing 25 ml of the respective liquid sealing products.

TABLE I

Stagnant Seal & Seal Rupture Test - 15 ml Seal Product

| | Product: | | | | | |
|---|---|---|---|---|---|---|
| | F-I | Duravit ® | Urilock ® | Falcon | BlueSeal ® | Control, No Seal |
| NH$_3$-ppm Stagnant Seal Test | 2.8 | 5.8 | 15.5 | 5.8 | 111.0 | 166.0 |
| NH$_3$-ppm Rupture Seal Test | 0.0 | 5.2 | 11.4 | 9.0 | 160.0 | 162.0 |
| Control, product only | 6.2 | 4.9 | 3.8 | 19.1 | 150.0 | |

TABLE II

Stagnant Seal & Seal Rupture Test - 25 ml Seal Product

| | Product | | | | | |
|---|---|---|---|---|---|---|
| | F-I | Duravit ® | Urilock ® | Falcon | BlueSeal ® | Control, No Seal |
| NH$_3$-ppm Stagnant Seal Test | 0.0 | 1.8 | 9.1 | 0.8 | 42.0 | 166.0 |

TABLE II-continued

Stagnant Seal & Seal Rupture Test - 25 ml Seal Product

| | F-I | Duravit ® | Urilock ® | Falcon | BlueSeal ® | Control, No Seal |
|---|---|---|---|---|---|---|
| NH₃-ppm Rupture Seal Test | 0.0 | 4.0 | 11.5 | 28.0 | 104.0 | 162.0 |
| Control, Product Only | 6.1 | 3.8 | 3.4 | 4.8 | 182.0 | |

A stagnant seal test "repeated" was also used to test the effectiveness of the urinal sealants. The stagnant seal test "repeated" test determines the seal's ability to prevent ammonia seepage through the seal when a waterless urinal sits unused for 48 hours. This test utilized color diffusion tubes for ammonia detection, manufactured by RAE Systems and commercially available from, for example, SKC, Inc., Eighty Four, Pa., and was carried out with 25 ml of sealing liquid. The liquid seal samples were sealed and a certified, low detection, passive color diffusion tube was inserted into the sealed head space of the sample. Used primarily in the area of worker safety, color diffusion tubes are manufactured as a low cost way to measure the airborne concentration of specific gases, including ammonia. As the ammonia gas diffuses through the tube, a visible indicator color change occurs that corresponds to a parts per million (ppm) calibration on the side of the tube. The ppm ammonia gas concentration can then be directly read from the side of the tube. Readings were taken every 12 hours to record how much cumulative ammonia gas had seeped through the seal and was present in the head space. All tubes were inserted at the same time point and were subjected to the same room temperature and humidity.

The seal rupture test "repeated" determined a seal's ability to repair itself and prevent seepage of ammonia through the seal after sitting still for 48 hours. Water streamed from a water bottle represented a urine stream that would disrupt the seal to simulate urinal use after sitting idle for 48 hours. This test utilized the PID meter for ammonia detection and was carried out with 25 ml of liquid sealant. This test was conducted on each seal after 48 hours of stagnant sitting. The stagnant seal was ruptured using the water stream from a water bottle in order to simulate a urine stream. This tested the seal's ability to repair itself from abrupt rupture. After rupturing the seal, the ammonia released into the head space was measured using a PID meter. Peak readings were observed, recorded and the test data was logged.

Example 3

TABLE III shows the results of 72 hour stagnant seal and seal rupture tests for the various liquid sealing products. The experimental protocols for these investigations used 15 ml of each respective liquid sealing product. TABLE IV is a summary of the data from the above-described experiments.

TABLE III

Stagnant Seal & Seal Rupture Test - 25 ml Seal Product

| | F-I | Duravit | Urilock ® | Falcon | BlueSeal ® | Control, No Seal |
|---|---|---|---|---|---|---|
| Day One | 0.0 | 20.0 | 9.1 | 5.0 | 23.0.0 | 166.0 |
| Day Two | 0.0 | 40.0 | 18.0 | 10.0 | 50.0 | |
| Day Three | 0.0 | 60.0 | 26.0 | 11.0 | 60.0.0 | |
| Rupture | 0.0 | 0.0* | 4.8 | 18.5 | 166.0 | 162.0 |

*NH₃ dissipated

TABLE IV

Stagnant Seal & Seal Rupture Test - 25 ml Seal Product

| | F-I | Duravit ® | Urilock ® | Falcon | BlueSeal ® | Control, No Seal |
|---|---|---|---|---|---|---|
| Stagnant 25 ml | 0.0 | 1.8 | 9.1 | 0.8 | 42.0 | 166.0 |
| Rupture 25 ml | 0.0 | 4.0 | 11.5 | 28.0 | 104.0 | 162.0 |
| Stagnant 15 ml | 2.8 | 5.8 | 15.5 | 5.8 | 111.0 | |
| Rupture 15 ml | 0.0 | 5.2 | 11.4 | 9.0 | 160.0 | |
| 48 Hour Stagnant | 0.0 | 60.0 | 26.0 | 11.0 | 60.0 | |
| 48 Hour Rupture | 0.0 | 0.0* | 4.8 | 18.5 | 166.0 | |

*NH₃ dissipated

TABLE V shows data from the experimental timeline described in the preceding paragraph for 25 ml of each of the liquid sealing products. Average PID readings for each measured time period, base line, zero, stagnant, and rupture, are given. TABLE VI illustrates selected data from an experimental timeline for an analogous experiment carried out with 15 ml of each liquid sealing product.

TABLE V

Stagnant Seal & Rupture Test Results (PID) (25 ml Test)

| Product | Sample time | PID Reading before NH₃ added | PID Reading after 25 ml NH₃ added | PID Reading during seal break test |
|---|---|---|---|---|
| Falcon | 9:20 am | 4.8 ppm | 0.8 ppm | 28.0 |
| Urilock ® | 10:13 am | 3.4 ppm | 9.1 ppm | 11.5 ppm |
| BlueSeal ® | 9:41 am | 182 ppm | 42 ppm | 104 ppm |
| Duravit ® | 8:47 am | 3.8 ppm | 1.8 ppm | 4.0 ppm |
| F-I | 10:40 am | 6.1 ppm | 0.0 ppm | 0.0 ppm |

TABLE VI

Stagnant Seal & Rupture Test Results (PID) (15 ml Test)

| Product | Sample time | PID Reading before NH₃ added | PID Reading after 25 ml NH₃ added | PID Reading during seal break test |
|---|---|---|---|---|
| Falcon | 12:55 pm | 19.1 ppm | 5.8 ppm | 9.0 |
| Urilock ® | 12:37 pm | 3.8 ppm | 15.5 ppm | 11.4 ppm |
| BlueSeal ® | 1:15 pm | 150 ppm | 111 ppm | 160 ppm |

TABLE VI-continued

Stagnant Seal & Rupture Test Results (PID) (15 ml Test)

| Product | Sample time | PID Reading before NH$_3$ added | PID Reading after 25 ml NH$_3$ added | PID Reading during seal break test |
|---|---|---|---|---|
| Duravit ® | 12:06 am | 4.9 ppm | 5.8 ppm | 5.2 ppm |
| F-I | 12:20 pm | 6.2 ppm | 2.8 ppm | 0.0 ppm |

Example 4

Stagnant seal and seal rupture tests were preformed with a further set of commercially available liquid urinal trap seals as shown in TABLE VII. This experiment was performed using 25 ml of seal liquid and the data were generated using PID methodology with the results given in ppm.

TABLE VII

Stagnant Seal & Seal Rupture Test—25 ml Seal Product

| | Product | | | | | |
|---|---|---|---|---|---|---|
| | F-I | Duravit ® | Zurn | Urilock ® | Falcon | BlueSeal ® | Control, No Seal |
| NH$_3$-ppm Stagnant Seal Test | 0.0 | 1.8 | 6.8 | 9.1 | 0.8 | 42.0 | 166.0 |
| NH$_3$-ppm Rupture Seal Test | 0.0 | 4.0 | 3.5 | 11.5 | 28.0 | 104 | 162.0 |
| Control, product only | 6.1 | 3.8 | 3.5 | 3.4 | 4.8 | 182.0 | |

Example 5

After further considering the dramatic results with respect to the formulation of the present invention compared to other commercially available urinal trap seals, the inventor concluded that adjusting the viscosity of a liquid trap seal to between 100 to 1000 centipoise (cP) and preferably 400 cP, has a beneficial effect on the maintenance and plasticity of the seal. The below experiment was performed in which a gellant was added to one of the poorer performing trap seals. This data is shown in TABLE VIII.

TABLE VIII

| Product | F-I (400 cP) | BlueSeal ® w/ gellant (350 cP) | BlueSeal ® (30 cP) | Control, No Seal |
|---|---|---|---|---|
| NH$_3$-ppm Stagnant Seal Test | 0.0 | 8.1 | 42.0 | 166.0 |
| NH$_3$-ppm Rupture Seal Test | 0.0 | 19.0 | 104.0 | 162.0 |
| Control, Product Only | 6.1 | 9.7 | 182.0 | |

As shown in TABLE VIII, by bringing the thickness of the commercially available product to the specified viscosity, its effectiveness was increased significantly. Based on this example and known methodologies to set and determine viscosity, a skilled artisan could determine the effective amount of gellant to be added to a liquid seal to achieve a viscosity of 100-1000 cP and preferably 400 cP.

The comparative data described herein clearly illustrates and demonstrates the utility of the liquid sealant claimed herein. In each test performed, the sealing product according to the invention outperformed the commercially-available liquid sealants. The present application is thusly applicable as a seal for waterless urinals and, as one of skill will recognize, various other analogous applications requiring an odor suppressing seal.

All publications, patents, and patent applications cited herein are hereby incorporated by reference in their entirety for all purposes. Nothing herein is to be construed as an admission that the invention is not entitled to antedate such disclosure by virtue of prior invention. Those skilled in the art will recognize, or be able to ascertain using no more then routine experimentation, numerous equivalents to the specific methods and compositions described herein. Such equivalents are considered to be within the scope of this invention and covered by the following claims. It is also to be understood that the terminology used herein is for the purpose of describing particular embodiments only, and is not intended to limit the scope of the present invention which will be limited only by the appended claims.

What is claimed is:

1. A method for suppressing odors from a waterless urinal, the method comprising the step of placing a liquid barrier sealant in a waterless urinal, the liquid barrier sealant comprising:
   a gellant;
   a glyceride mixed with the gellant to form the liquid barrier sealant;
   wherein the liquid barrier sealant is self-repairable after being ruptured; and wherein the viscosity of the liquid barrier sealant is higher when it is stagnant than when it is ruptured.

2. The method of claim 1 wherein the gellant is a polyamide-based gellant.

3. The method of claim 1 wherein the gellant is from about 1 to about 50 weight percent of the liquid barrier sealant.

4. The method of claim 1 wherein the glyceride is in the form of a vegetable oil.

5. The method of claim 4 wherein the vegetable oil is selected from the group consisting of almond oil, canola oil, corn oil, cottonseed oil, flaxseed oil, grape seek oil, olive oil, palm oil, peanut oil, safflower oil, sesame oil, soybean oil, sunflower oil, walnut oil, and mixtures thereof.

6. The method of claim 1 wherein the glyceride is from about 50 to about 99 weight percent of the liquid barrier sealant.

7. The method of claim 1 wherein the liquid barrier sealant further includes an odor control agent.

8. The method of claim 1 wherein the liquid barrier sealant further includes a fragrance.

9. The method of claim 1 wherein the liquid barrier sealant further includes a preservative.

10. The method of claim 1 wherein the liquid barrier sealant further includes an anti-stick agent.

11. The method of claim 1 wherein the liquid barrier sealant further includes a dye.

12. The method of claim 1 wherein the liquid barrier sealant includes a blend of a dye, a fragrance, a preservative, an anti-stick agent, and an odor control agent, with the dye about 0.1 weight percent of the liquid barrier sealant, the fragrance about 2 weight percent of the liquid barrier sealant, the preservative about 1 weight percent of the liquid barrier sealant, the anti-stick agent about 2 weight percent of the liquid barrier sealant, and the odor control agent about 1 weight percent of the liquid barrier sealant.

13. A method for suppressing odors from a drain, the method comprising the step of placing a drain trap sealant in a trapway of a drain, the drain trap sealant comprising:
- a gellant;
- a glyceride mixed with the gellant to form the liquid barrier sealant;
- wherein the drain trap sealant is self-repairable after being ruptured; and
- wherein the viscosity of the drain trap sealant is higher when it is stagnant than when it is ruptured.

\* \* \* \* \*